US008496662B2

(12) United States Patent
Novak et al.

(10) Patent No.: US 8,496,662 B2
(45) Date of Patent: Jul. 30, 2013

(54) METHOD AND APPARATUS FOR FORMING A WEDGE-LIKE OPENING IN A BONE FOR AN OPEN WEDGE OSTEOTOMY

(75) Inventors: Vincent P. Novak, Longmont, CO (US); Kelly Ammann, Boulder, CO (US); Dennis McDevitt, Raleigh, NC (US)

(73) Assignee: Arthrex, Inc., Naples, FL (US)

( * ) Notice: Subject to any disclaimer, the term of this patent is extended or adjusted under 35 U.S.C. 154(b) by 1082 days.

(21) Appl. No.: 11/350,333

(22) Filed: Feb. 8, 2006

(65) Prior Publication Data
US 2006/0241636 A1 Oct. 26, 2006

Related U.S. Application Data

(63) Continuation-in-part of application No. 11/047,159, filed on Jan. 31, 2005, and a continuation-in-part of application No. 11/047,551, filed on Jan. 31, 2005, now Pat. No. 8,083,746.

(60) Provisional application No. 60/651,086, filed on Feb. 8, 2005.

(51) Int. Cl.
*A61B 17/56* (2006.01)
(52) U.S. Cl.
USPC ............................................................ 606/87
(58) Field of Classification Search
USPC .................................................... 606/87–89
See application file for complete search history.

(56) References Cited

U.S. PATENT DOCUMENTS

| | | | |
|---|---|---|---|
| 2,737,724 A | 3/1956 | Herz |
| 3,579,777 A | 5/1971 | Milewski |
| 3,750,652 A | 8/1973 | Sherwin |
| 4,349,018 A | 9/1982 | Chambers |
| 4,421,112 A | 12/1983 | Mains et al. |
| 4,501,268 A | 2/1985 | Comparetto |
| 4,523,587 A | 6/1985 | Frey |
| 4,563,489 A | 1/1986 | Urist |
| 4,565,191 A | 1/1986 | Slocum |
| 4,750,481 A | 6/1988 | Reese |
| 4,769,040 A | 9/1988 | Wevers |
| 4,817,794 A | 4/1989 | Workman |
| 4,851,005 A | 7/1989 | Hunt et al. |

(Continued)

FOREIGN PATENT DOCUMENTS

| | | |
|---|---|---|
| CN | 1132067 | 10/1996 |
| CN | 1181696 | 5/1998 |

(Continued)

OTHER PUBLICATIONS

Oliver C. Kessler et al., Avoidance of Medial Cortical Fracture in High Tibial Osteotomy: Improved Technique, Clinical Orthopaedics and Related Research, Feb. 2002, pp. 180-185, No. 395.

(Continued)

*Primary Examiner* — Ellen C Hammond
*Assistant Examiner* — Jacqueline Johanas
(74) *Attorney, Agent, or Firm* — Dickstein Shapiro LLP

(57) ABSTRACT

The present application provides an apparatus for forming and method of creating a wedge-like opening in a bone for an open wedge osteotomy by identifying a cutting plane through the bone; and inserting an apex pin along the cutting plane to limit cutting and minimize stress risers in the bone.

11 Claims, 27 Drawing Sheets

LEFT LEG
ANTERO-MEDIAL VIEW

U.S. PATENT DOCUMENTS

| | | | |
|---|---|---|---|
| 4,852,558 A | 8/1989 | Outerbridge | |
| 4,892,093 A | 1/1990 | Zarnowski et al. | |
| 4,936,844 A | 6/1990 | Chandler et al. | |
| 4,961,740 A | 10/1990 | Ray et al. | |
| 5,053,039 A | 10/1991 | Hofmann et al. | |
| 5,246,444 A * | 9/1993 | Schreiber | 606/87 |
| 5,254,119 A | 10/1993 | Schreiber | |
| 5,275,603 A | 1/1994 | Ferrante et al. | |
| 5,297,538 A | 3/1994 | Daniel | |
| 5,306,276 A | 4/1994 | Johnson et al. | |
| 5,352,229 A | 10/1994 | Goble et al. | |
| 5,364,402 A * | 11/1994 | Mumme et al. | 606/88 |
| 5,413,579 A | 5/1995 | Du Toit | |
| 5,445,640 A | 8/1995 | Johnson et al. | |
| 5,451,228 A | 9/1995 | Johnson et al. | |
| 5,540,695 A | 7/1996 | Levy | |
| 5,569,250 A | 10/1996 | Sarver et al. | |
| 5,601,565 A * | 2/1997 | Huebner | 606/87 |
| 5,609,635 A | 3/1997 | Michelson | |
| 5,613,969 A | 3/1997 | Jenkins, Jr. | |
| 5,620,448 A | 4/1997 | Puddu | |
| 5,640,813 A | 6/1997 | Glazik et al. | |
| 5,662,655 A | 9/1997 | Laboureau et al. | |
| 5,669,909 A | 9/1997 | Zdeblick et al. | |
| 5,674,296 A | 10/1997 | Bryan et al. | |
| 5,681,316 A | 10/1997 | DeOrio et al. | |
| 5,722,978 A | 3/1998 | Jenkins, Jr. | |
| 5,733,290 A | 3/1998 | McCue et al. | |
| 5,749,875 A * | 5/1998 | Puddu | 606/87 |
| 5,766,251 A | 6/1998 | Koshino | |
| 5,843,085 A | 12/1998 | Graser | |
| 5,888,223 A | 3/1999 | Bray, Jr. | |
| 5,911,724 A | 6/1999 | Wehrli | |
| 5,980,526 A | 11/1999 | Johnson et al. | |
| 6,008,433 A | 12/1999 | Stone | |
| 6,027,504 A | 2/2000 | McGuire | |
| 6,039,761 A | 3/2000 | Li et al. | |
| 6,086,593 A | 7/2000 | Bonutti | |
| 6,099,531 A | 8/2000 | Bonutti | |
| 6,102,950 A | 8/2000 | Vaccaro | |
| 6,190,390 B1 | 2/2001 | McAllister | |
| 6,200,347 B1 | 3/2001 | Anderson et al. | |
| 6,203,546 B1 | 3/2001 | MacMahon | |
| 6,214,007 B1 | 4/2001 | Anderson | |
| 6,224,599 B1 | 5/2001 | Baynham et al. | |
| 6,264,694 B1 | 7/2001 | Weiler | |
| 6,277,149 B1 | 8/2001 | Boyle et al. | |
| 6,287,308 B1 | 9/2001 | Betz et al. | |
| 6,379,361 B1 | 4/2002 | Beck, Jr. et al. | |
| 6,423,063 B1 | 7/2002 | Bonutti | |
| 6,461,359 B1 | 10/2002 | Tribus et al. | |
| 6,478,800 B1 | 11/2002 | Fraser et al. | |
| 6,544,266 B1 * | 4/2003 | Roger et al. | 606/70 |
| 6,565,570 B2 | 5/2003 | Sterett et al. | |
| 6,575,982 B1 | 6/2003 | Bonutti | |
| 6,699,252 B2 | 3/2004 | Farr, II et al. | |
| 6,743,255 B2 | 6/2004 | Ferree | |
| 6,755,841 B2 | 6/2004 | Fraser et al. | |
| 6,796,986 B2 | 9/2004 | Duffner | |
| 6,823,871 B2 * | 11/2004 | Schmieding | 128/898 |
| 7,318,827 B2 * | 1/2008 | Leitner et al. | 606/87 |
| 8,298,238 B2 * | 10/2012 | Haines | 606/87 |
| 2001/0029375 A1 * | 10/2001 | Betz et al. | 606/61 |
| 2002/0010513 A1 | 1/2002 | Schmieding | |
| 2002/0029084 A1 | 3/2002 | Paul et al. | |
| 2002/0095156 A1 | 7/2002 | Kuras et al. | |
| 2002/0165552 A1 * | 11/2002 | Duffner | 606/87 |
| 2003/0028197 A1 | 2/2003 | Hanson et al. | |
| 2003/0105526 A1 | 6/2003 | Bryant et al. | |
| 2003/0171757 A1 | 9/2003 | Coon et al. | |
| 2003/0195516 A1 | 10/2003 | Sterett et al. | |
| 2003/0199881 A1 | 10/2003 | Bonutti | |
| 2004/0039387 A1 | 2/2004 | Gause et al. | |
| 2005/0075641 A1 | 4/2005 | Singhatat et al. | |
| 2005/0154394 A1 * | 7/2005 | Michalowicz | 606/87 |
| 2005/0216090 A1 | 9/2005 | O'Driscoll et al. | |
| 2005/0228498 A1 | 10/2005 | Andres | |
| 2005/0251147 A1 | 11/2005 | Novak | |
| 2005/0273114 A1 | 12/2005 | Novak | |
| 2005/0273115 A1 | 12/2005 | Coon et al. | |
| 2006/0106396 A1 | 5/2006 | Justin et al. | |
| 2006/0122617 A1 | 6/2006 | Lavallee et al. | |
| 2006/0129163 A1 | 6/2006 | McGuire | |
| 2006/0149274 A1 | 7/2006 | Justin et al. | |
| 2006/0149275 A1 | 7/2006 | Cadmus | |
| 2006/0217808 A1 | 9/2006 | Novak et al. | |
| 2007/0016209 A1 | 1/2007 | Ammann et al. | |
| 2008/0015604 A1 * | 1/2008 | Collazo | 606/87 |
| 2009/0076512 A1 * | 3/2009 | Ammann et al. | 606/87 |
| 2009/0076514 A1 * | 3/2009 | Haines | 606/88 |
| 2010/0152782 A1 * | 6/2010 | Stone et al. | 606/280 |

FOREIGN PATENT DOCUMENTS

| | | |
|---|---|---|
| EP | 1 099 428 | 5/2001 |
| EP | 1669033 | 6/2006 |
| FR | 2741525 | 5/1997 |
| FR | 2 764 183 | 12/1998 |
| WO | WO 96/14802 | 5/1996 |
| WO | WO 99/52473 | 10/1999 |
| WO | WO 2005/048888 | 6/2005 |
| WO | WO 2006/107800 | 10/2006 |

OTHER PUBLICATIONS

Sohn, Meniscus Transplantation: Current Concepts, The Journal of Knee Surgery, Apr. 2008, pp. 163-172, vol. 21, No. 2.

* cited by examiner

LEFT LEG

METHOD AND APPARATUS FOR FORMING A WEDGE-LIKE OPENING IN A BONE FOR AN OPEN WEDGE OSTEOTOMY

REFERENCE TO PENDING PRIOR PATENT APPLICATIONS

This patent application:

(i) is a continuation-in-part of pending prior U.S. patent application Ser. No. 11/047,159, filed Jan. 31, 2005 by Vincent P. Novak for OPEN WEDGE OSTEOTOMY SYSTEM AND SURGICAL METHOD;

(ii) is a continuation-in-part of pending prior U.S. patent application Ser. No. 11/047,551 NOW U.S. Pat. No. 8,083, 746, filed Jan. 31, 2005 by Vincent P. Novak for OPEN WEDGE OSTEOTOMY SYSTEM AND SURGICAL METHOD; and (iii) claims benefit of pending prior U.S. Provisional Patent Application Ser. No. 60/651,086, filed Feb. 8, 2005 by Vincent P. Novak et al. for OPEN WEDGE OSTEOTOMY SYSTEM AND SURGICAL METHOD.

The three above-identified patent applications are hereby incorporated herein by reference.

FIELD OF THE INVENTION

This invention relates to surgical methods and apparatus in general, and more particularly to surgical methods and apparatus for performing open wedge osteotomies of the knee.

BACKGROUND OF THE INVENTION

Osteotomies of the knee are an important technique for treating knee osteoarthritis. In essence, knee osteotomies adjust the geometry of the knee joint so as to transfer weight bearing load from arthritic portions of the joint to the relatively unaffected portions of the joint.

Most knee osteotomies are designed to modify the geometry of the upper tibia, so as to adjust the manner in which the tibia engages the femur and hence the locations at which the load is transferred across the joint.

There are essentially two ways in which to adjust the orientation of the tibia: (i) the closed wedge technique; and (ii) the open wedge technique.

With the closed wedge technique, a wedge of bone is removed from the tibia, and the portions on either side of the resulting gap are brought together, whereby to reorient the tibial plateau and hence adjust the manner in which the tibia engages the femur.

With the open wedge technique, a cut is made into the tibia, the portions on either side of the cut are moved apart so as to form a wedge-like opening in the bone, and then the bone is secured in this position (e.g., by screwing metal plates to the bone or by inserting a wedge-shaped implant into the opening in the bone), whereby to reorient the tibial plateau and hence adjust the manner in which the tibia engages the femur.

While both closed wedge osteotomies and open wedge osteotomies provide substantial benefits to the patient, they are procedurally challenging to the surgeon. Among other things, with respect to open wedge osteotomies, it can be difficult to form the wedge-like opening in the bone with the necessary precision and with minimum trauma to the surrounding tissue.

The present invention is directed to open wedge osteotomies, and to a new method and apparatus for forming the wedge-like opening in the tibia.

SUMMARY OF THE INVENTION

The present invention comprises a novel method and apparatus for forming a wedge-like opening in the tibia for an open wedge knee osteotomy. More particularly, the present invention comprises the provision and use of a novel method and apparatus for forming a wedge-like opening in the tibia, utilizing an antero-medial approach, for an open wedge knee osteotomy.

In one form of the present invention, there is provided an apparatus for forming a wedge-like opening in a bone for an open wedge osteotomy, the apparatus comprising:

targeting apparatus for identifying a cutting plane through the bone and a boundary line for terminating a cut made along the cutting plane, wherein the boundary line is located within the bone; and an apex pin for disposition along the boundary line for providing (i) a positive stop at the boundary line for limiting cutting along the cutting plane, and (ii) a cylindrical opening extending along the boundary line so as to minimize the occurrence of stress risers within the bone when the bone on either side of the cut is moved apart so as to form the wedge-like opening in the bone.

In another form of the present invention, there is provided a method for forming a wedge-like opening in a bone for an open wedge osteotomy, the method comprising:

positioning targeting apparatus relative to the bone, so as to identify a cutting plane through the bone and a boundary line for terminating a cut made along the cutting plane, wherein the boundary line is located within the bone; and positioning an apex pin along the boundary line so as to provide (i) a positive stop at the boundary line for limiting cutting along the cutting plane, and (ii) a cylindrical opening extending along the boundary line so as to minimize the occurrence of stress risers within the bone when the bone on either side of the cut is moved apart so as to form the wedge-like opening in the bone;

cutting the bone along the cutting plane, with the cut terminating at the boundary line; and moving the bone on either side of the cut apart so as to form the wedge-like opening in the bone.

In another form of the present invention, there is provided a method for forming a wedge-like opening in a tibia for an open wedge osteotomy, the method comprising:

locating a positioning guide about the tibia so as to define the anterior-posterior tibial slope, a cutting plane extending through the tibia and a boundary line for terminating a cut make along the cutting plane, with the boundary line defining a bone hinge line;

inserting an apex pin through the positioning guide and along the boundary line;

mounting a cutting guide onto the positioning guide so that a cutting slot in the cutting guide is aligned co-planar with the cutting plane;

making an osteotomy cut along the cutting plane up to the boundary line; and moving the bone on either side of the cut apart so as to form the wedge-like opening in the bone.

In another form of the present invention, there is provided a method for forming a wedge-like opening in a tibia for an open wedge osteotomy, the method comprising:

locating a positioning guide about the medial aspect of the tibia so as to encompass a portion of the tibia, with a top edge of the positioning guide being positioned relative to the tibial plateau;

placing a first straight pin through the positioning guide and into the tibia so as to pivotally secure the positioning guide to the tibia;

rotating the positioning guide about the first pin until the top edge of the positioning guide is parallel to the anterior-posterior tibial slope;

placing a second pin through the positioning guide and into the tibia so as to secure the positioning guide to the tibia, with the positioning guide defining the anterior-posterior tibial slope, a cutting plane extending through the tibia and a boundary line for terminating a cut made along the cutting plane, with the boundary line defining a bone hinge line;

inserting an apex pin through the positioning guide and along the boundary line;

mounting a cutting guide onto the positioning guide so that a cutting slot in the cutting guide is aligned co-planar with the cutting plane;

making an osteotomy cut along the cutting plane up to the boundary line; and moving the bone on either side of the cut apart so as to form the wedge-like opening in the bone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Overview

Figure 1:
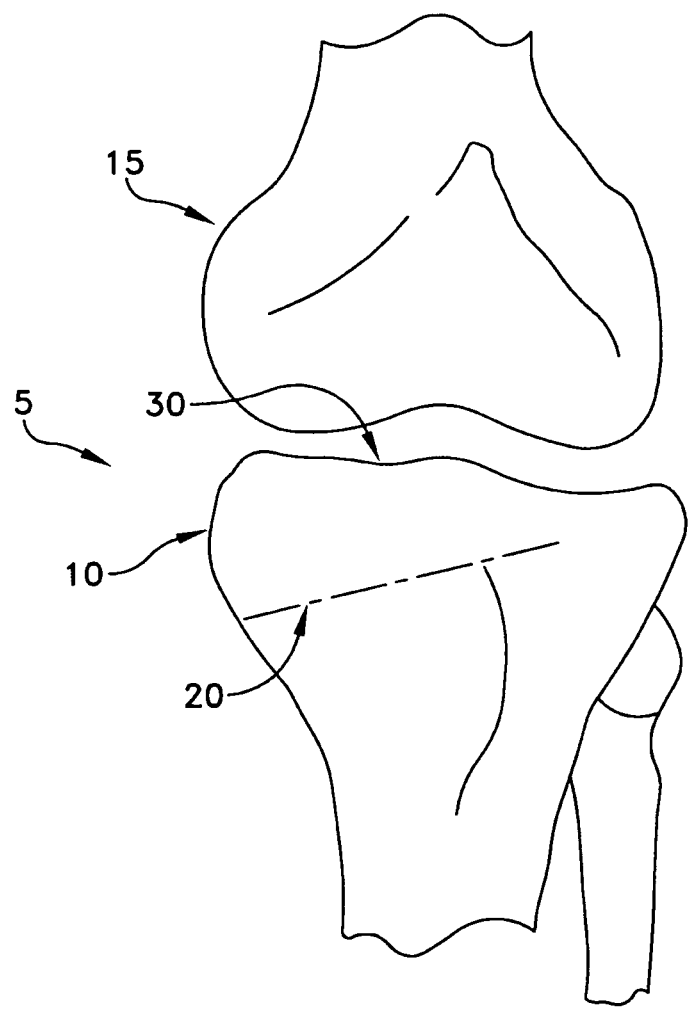
FIGS. 1-3 are schematic views showing the formation of a wedge-like opening in the tibia for an open wedge osteotomy, and positioning of a wedge-shaped implant into the wedge-like opening in the tibia.
Figure 2:
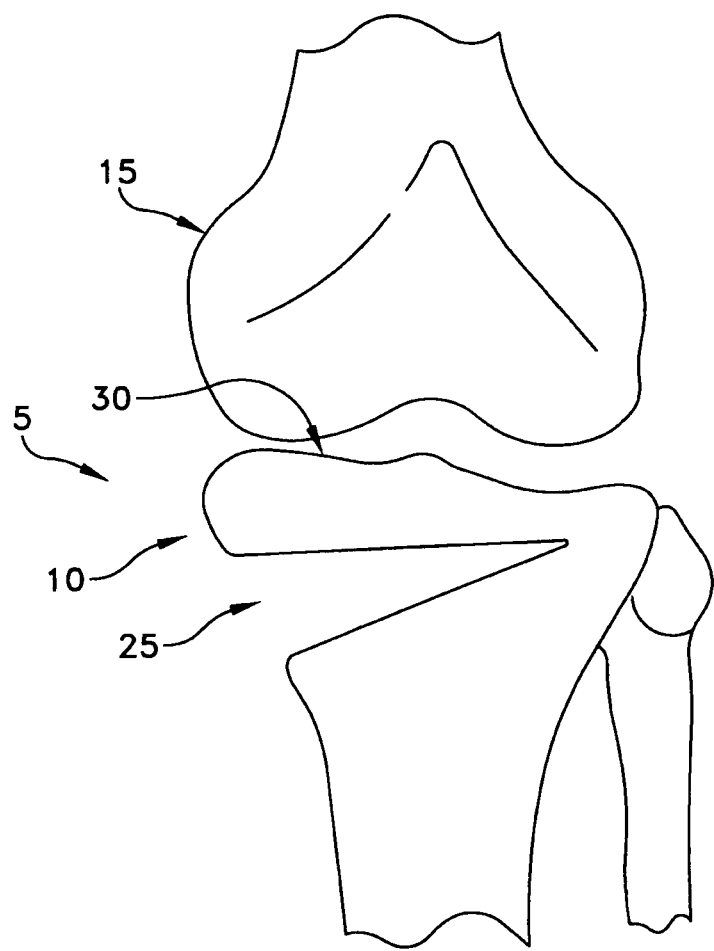
Figure 3:
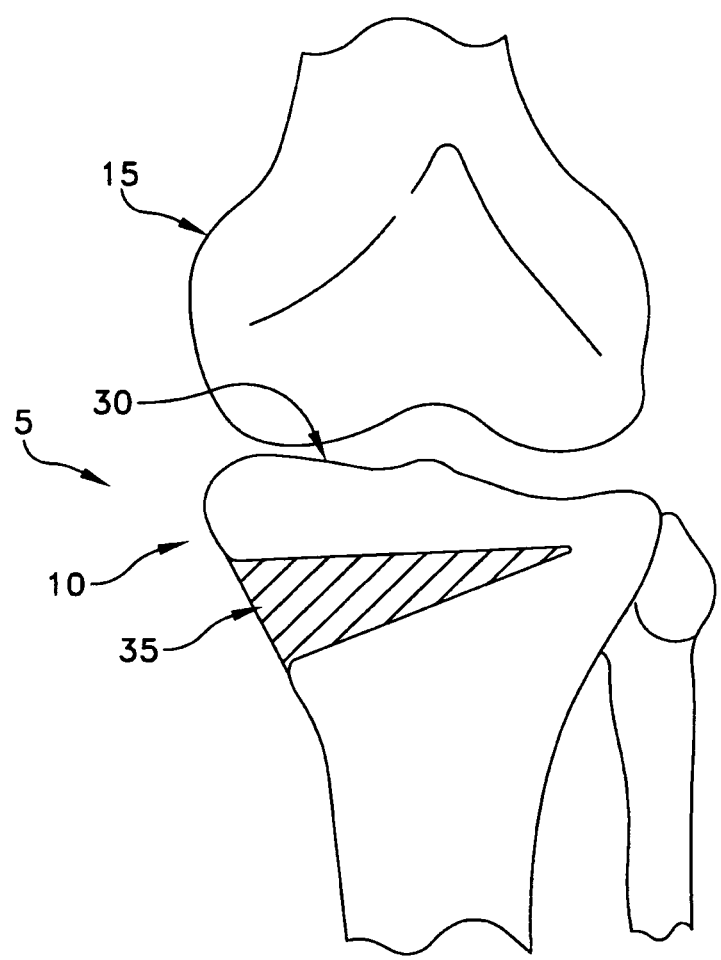

Looking first at FIGS. 1-3, there is shown a knee joint 5 upon which an open wedge osteotomy is to be performed. Knee joint 5 generally comprises a tibia 10 and a femur 15. In accordance with the present invention, the open wedge osteotomy is effected by first making a cut 20 (FIG. 1) into the upper tibia, and then moving apart the portions of the bone on either side of cut 20 so as to form a wedge-like opening 25 (FIG. 2) in the bone, with the wedge-like opening 25 being configured such that the tibial plateau 30 is given the desired orientation relative to femur 15. Cut 20 and wedge-like opening 25 may be formed in a variety of ways well known in the art.

The present invention provides a new and improved method and apparatus for forming cut 20 and wedge-like opening 25 using an antero-medial approach, as will be discussed in detail below.

Once the desired wedge-like opening 25 has been formed in tibia 10 and tibial plateau 30 given its desired orientation, the bone may be secured in position in a variety of ways well known in the art (e.g., by screwing metal plates to the bone or by inserting a wedge-shaped implant into the opening in the bone), whereby to reorient the tibial plateau and hence adjust the manner in which the tibia engages the femur. By way of example, FIG. 3 shows a wedge-shaped implant 35 inserted into the wedge-like opening formed in the tibia.

Discussion of the Relevant Planar Surfaces in a High Tibial Osteotomy

In order to appreciate certain aspects of the present invention, it is helpful to have a thorough understanding of the planar surfaces of the tibia that are relevant in performing a high tibial osteotomy. Thus, the following discussion presents a geometric description of the planar surfaces that are relevant to an open-wedge, high tibial osteotomy.

Figure 4:
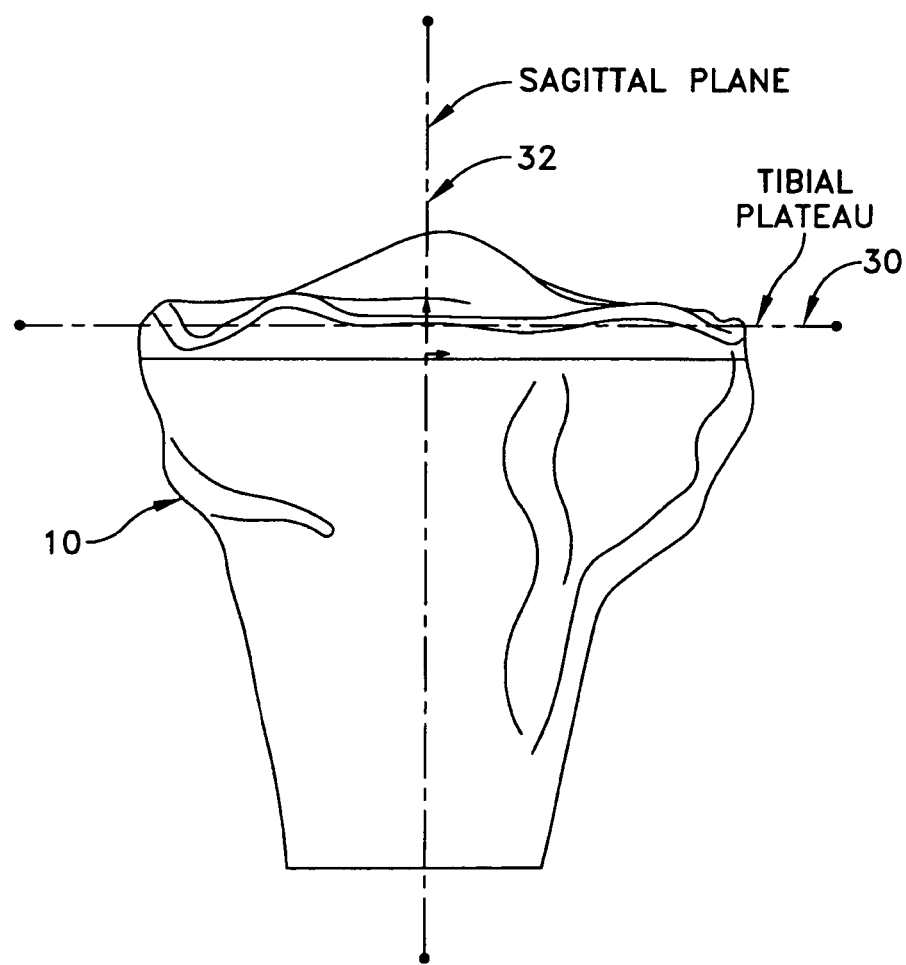
FIGS. 4-9 show the relevant planar surfaces in a high tibial osteotomy.
Figure 5:
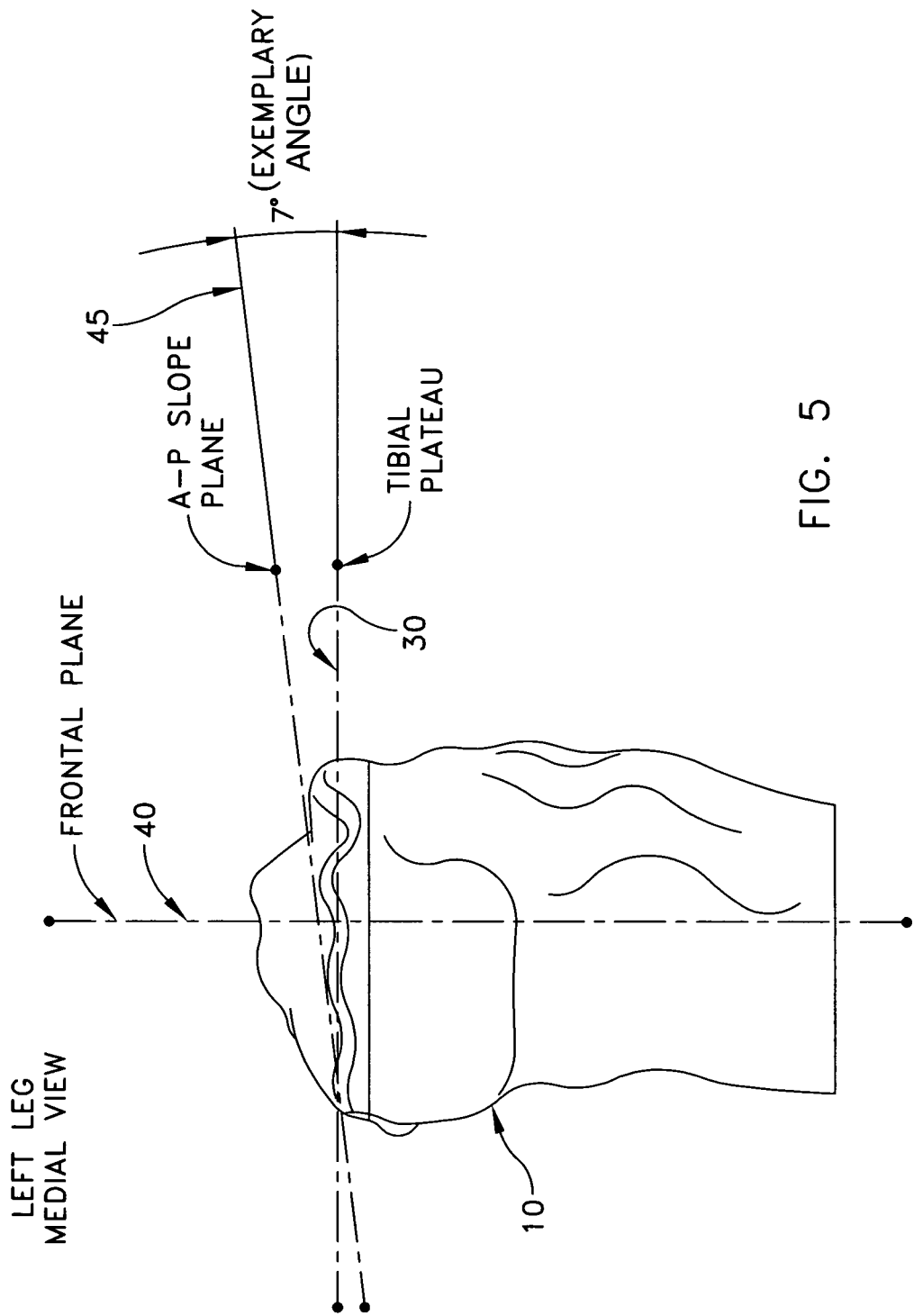

More particularly, and looking now at FIG. 4, the tibial plateau 30 may be described as a horizontal (or transverse) plane that intersects the superior surface of tibia 10. For reference, the sagittal plane 32 is also shown. As seen in FIG. 5, tibial plateau 30 is also perpendicular to the frontal plane 40. The anterior-posterior (A-P) slope is defined by an anterior-posterior (A-P) slope plane 45 that intersects the sloping surface of the tibia from anterior to posterior. Published research has demonstrated that the anterior-posterior slope is typically at an angle of approximately 7° to 11° to the tibial plateau 30; however, the specific angle may vary from individual to individual.

Figure 6:
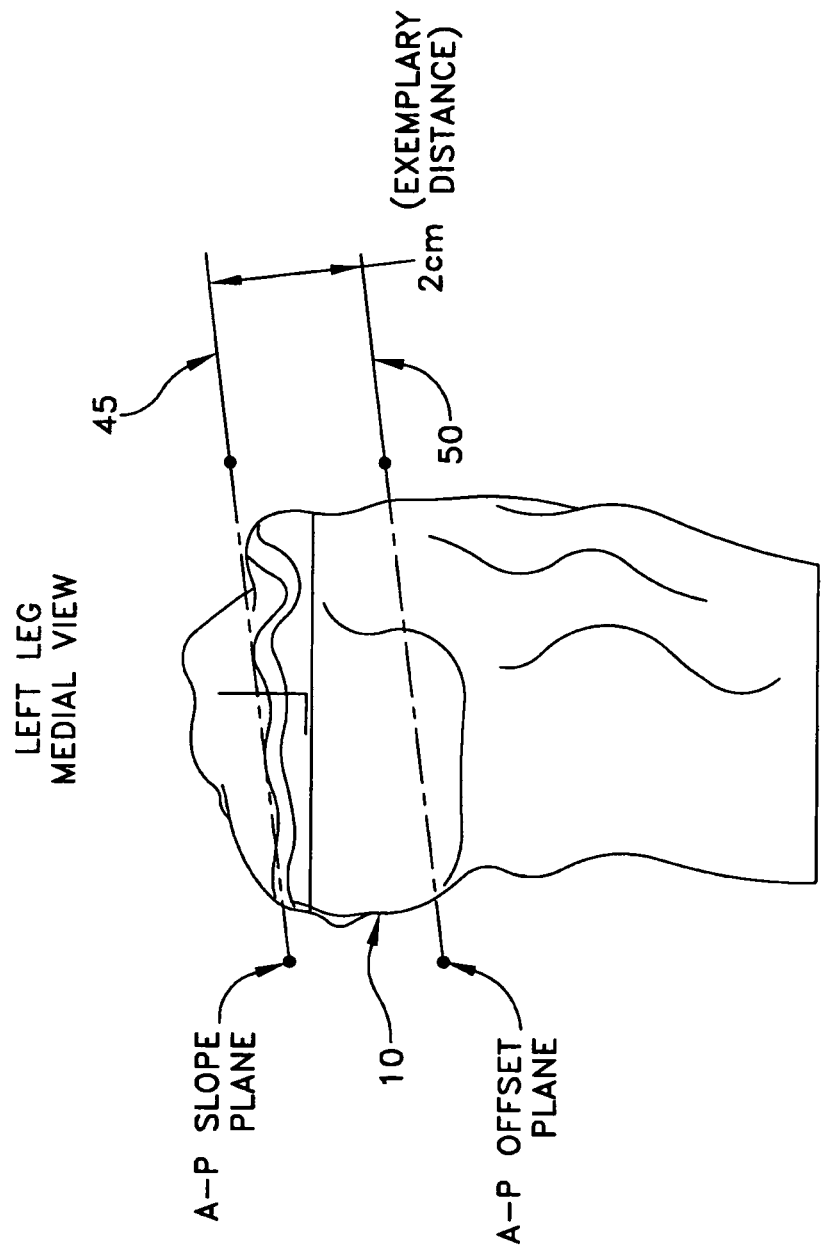

Looking next at FIG. 6, for a high tibial osteotomy, it is typical to stay about 2 cm inferior to the A-P slope plane 45. This offset can be referred to as the A-P offset plane 50.

Figure 7:
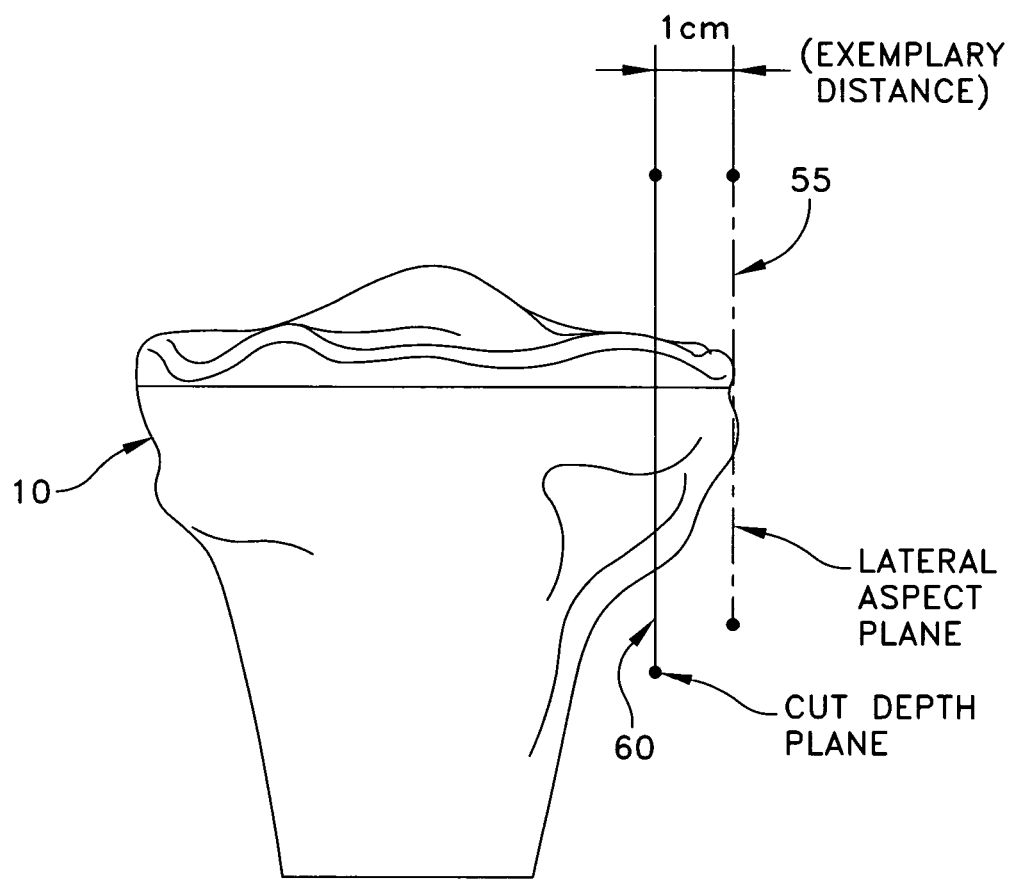

As seen in FIG. 7, the lateral aspect and cut depth may be defined by a lateral aspect plane 55 and a cut depth plane 60, with the cut depth being about 1 cm medial to the lateral aspect of the tibia.

Figure 8:
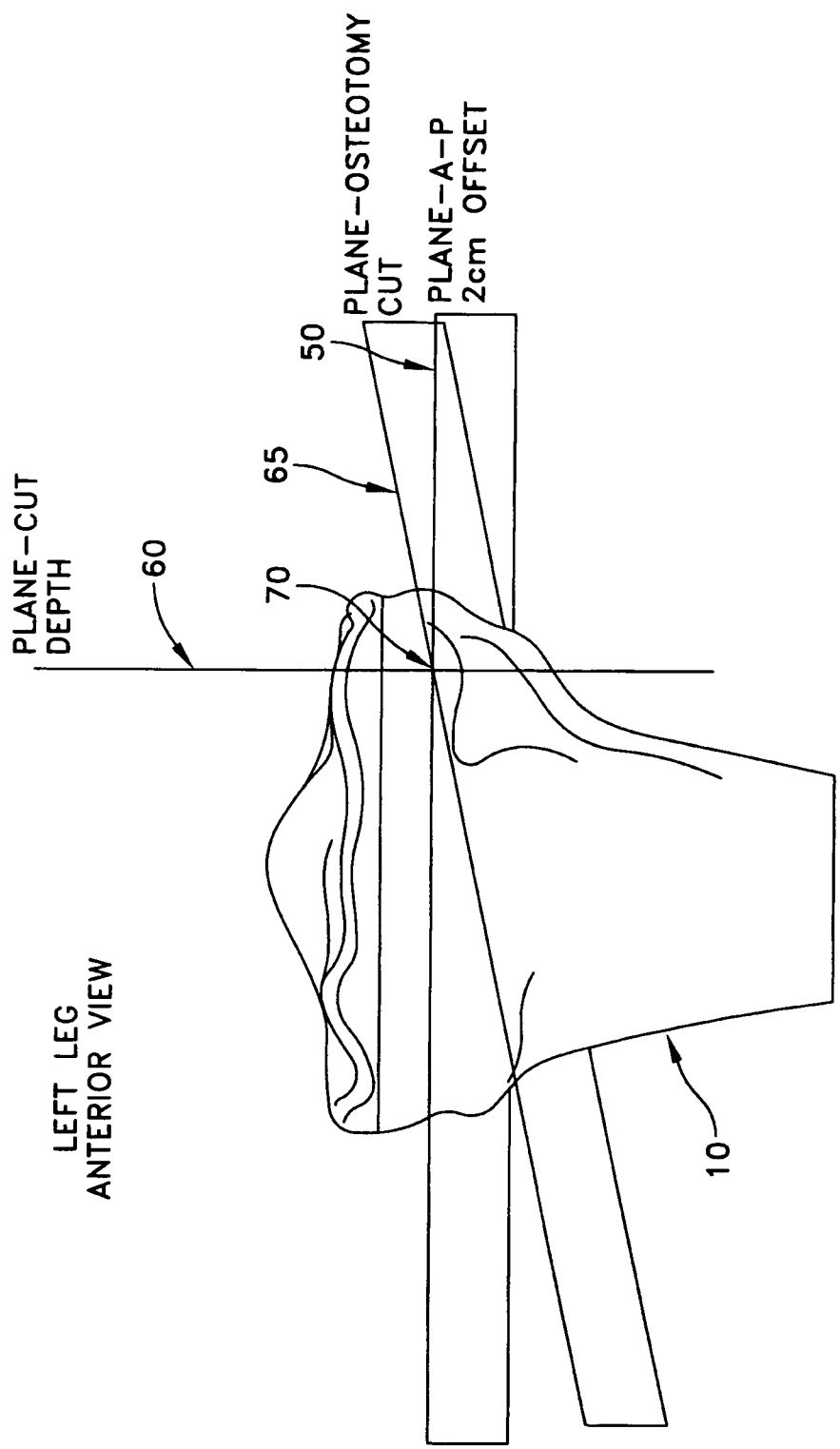

Looking next at FIG. 8, the osteotomy cut plane 65 (when seen from the direct frontal view) is formed by a plane that is rotated away from the A-P offset plane 50 through an axis formed by the intersection of the cut depth plane 60 and the A-P offset plane 50. It should be noted that the planes are "tilted" slightly when seen from the direct frontal view, since they follow the tilt of the A-P slope plane 45 (FIG. 6). The intersection of the A-P offset plane 50 and the cut depth plane 60 forms an axis 70 at the end of the osteotomy cut. In other words, the axis 70 defines a line through the tibia, co-planar with the osteotomy cut plane 65, which defines the furthest extent of the osteotomy cut into the tibia.

Figure 9:
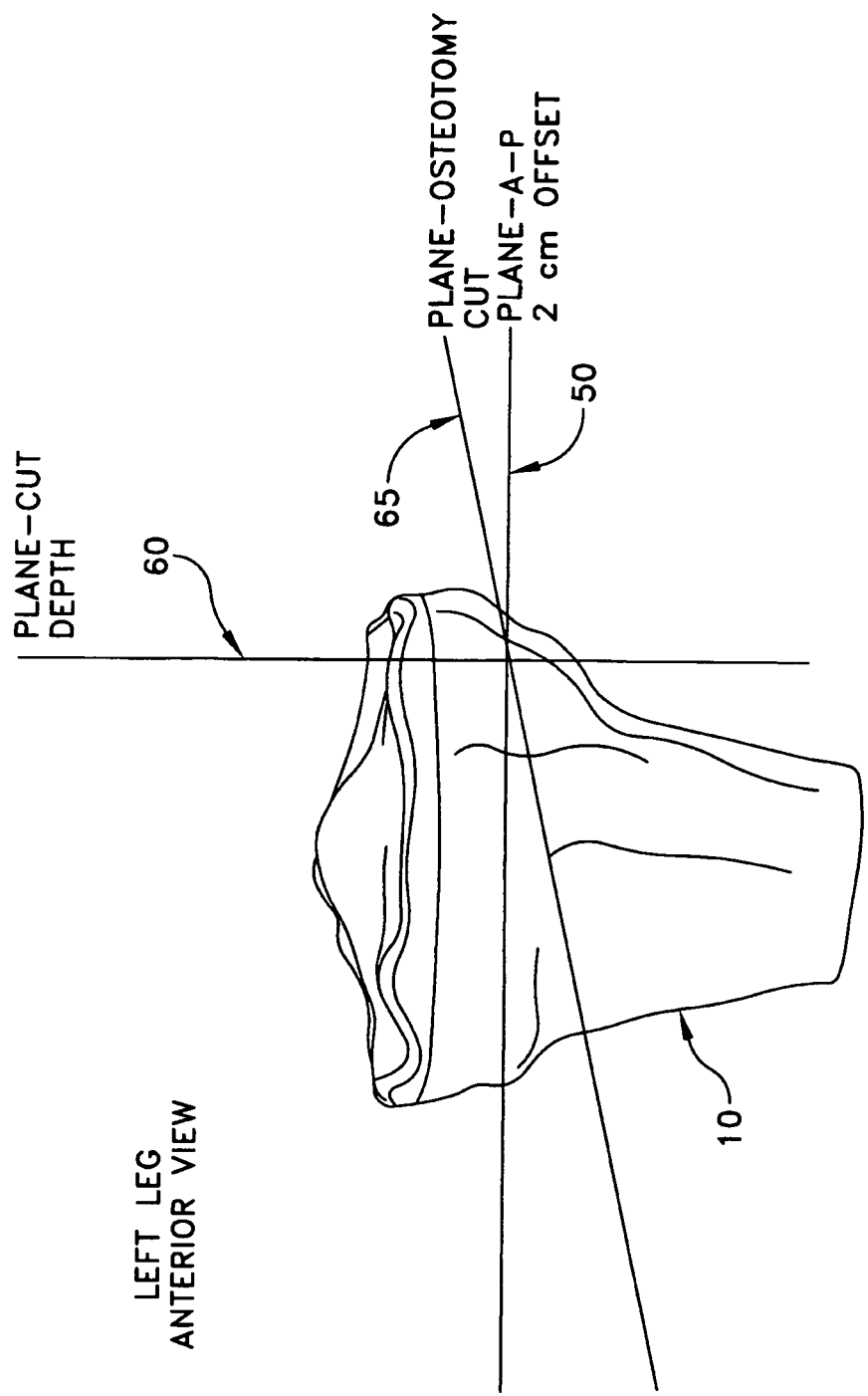

As seen in FIG. 9, the direct A-P view of the osteotomy plane is a direct view in line with the osteotomy. This view is tilted downward (i.e., at approximately 7°) from the direct frontal view. Again, the angle of tilt downward is equal to the A-P slope.

Figure 18:
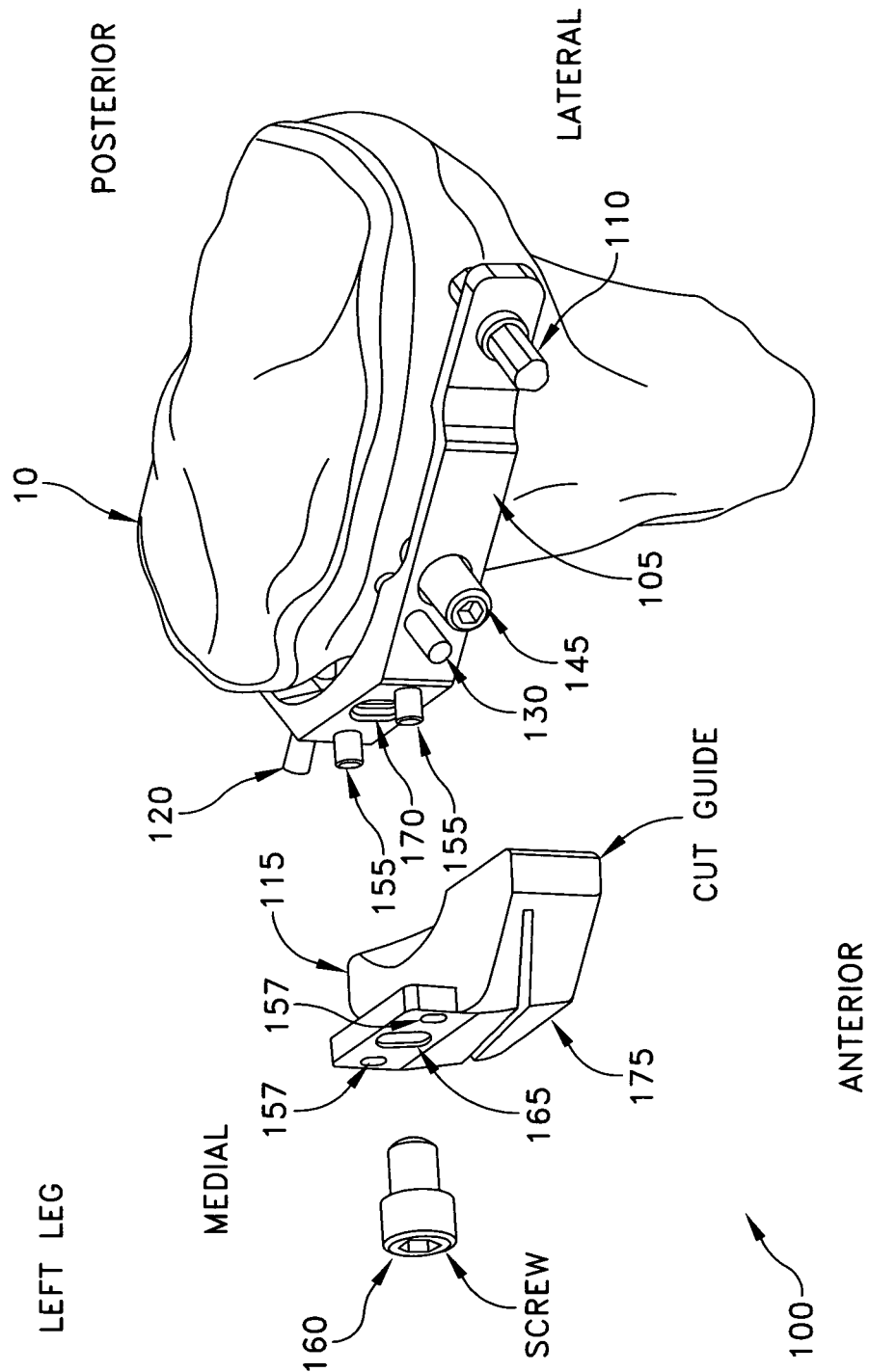
Figure 19:
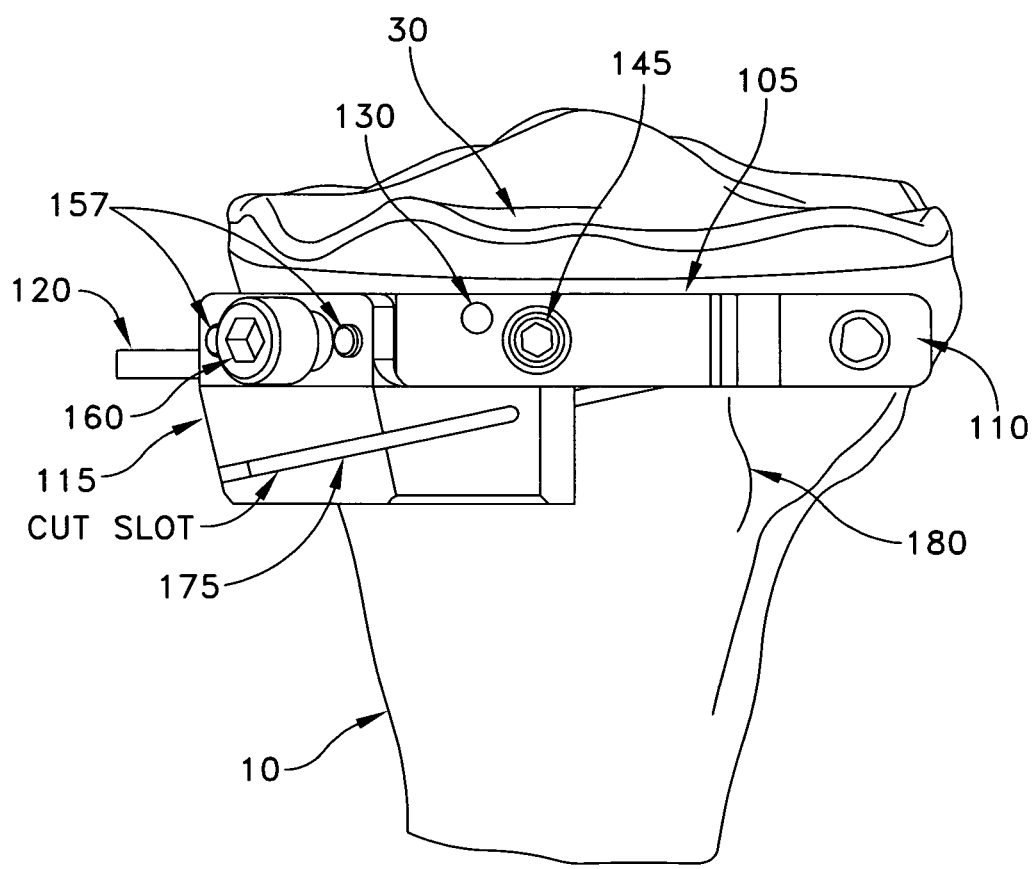
Figure 20:
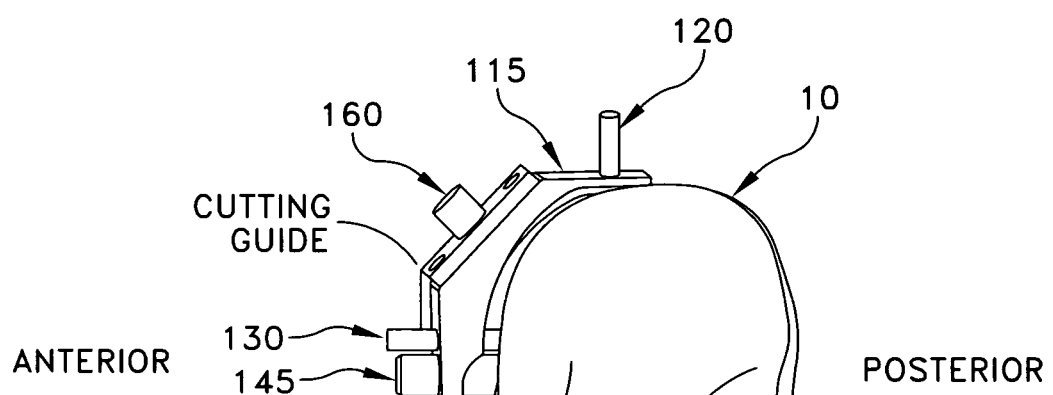

Novel Method and Apparatus for Forming an Antero-Medial Wedge-Like Opening in the Tibia In one preferred embodiment of the present invention, there is provided a novel osteotomy system 100 (FIG. 18) which is intended for use in making precise and repeatable osteotomy cuts for high tibial osteotomies using an antero-medial approach. System 100 generally comprises a positioning guide 105, an apex pin 110 and a cutting guide 115, and will hereinafter be discussed in further detail.

System 100 is intended to be located relative to the medial aspect of the tibia, parallel to the anterior-posterior (A-P) slope of the tibia and parallel to the tibial plateau, with the apex pin extending through the tibia along axis 70, i.e., at the position which will become the base or lateral hinge of the osteotomy cut, as will hereinafter be discussed in further detail.

Figure 10:
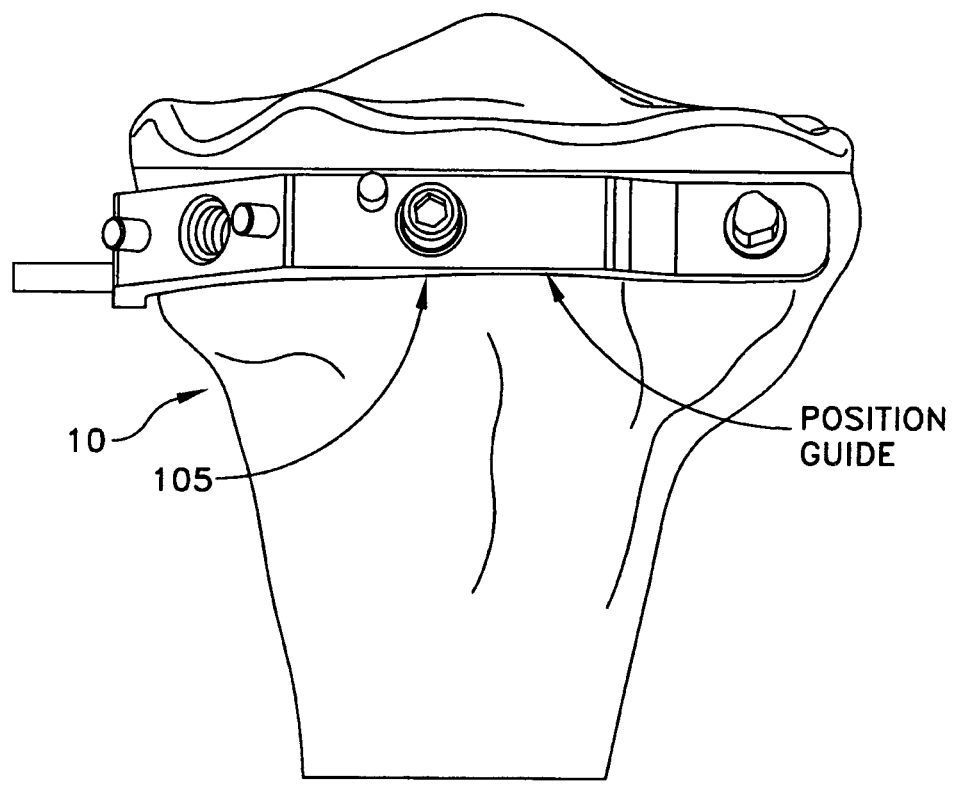
FIGS. 10-23 show one preferred method and apparatus for performing a high tibial osteotomy in accordance with the present invention.

Looking next at FIG. 10, the positioning guide 105 is positioned about the upper end of tibia 10 such that the positioning guide wraps around the medial aspect of the tibia. It should be appreciated that the positioning guide 105 does not necessarily need to be in contact with the tibia.

Figure 11:
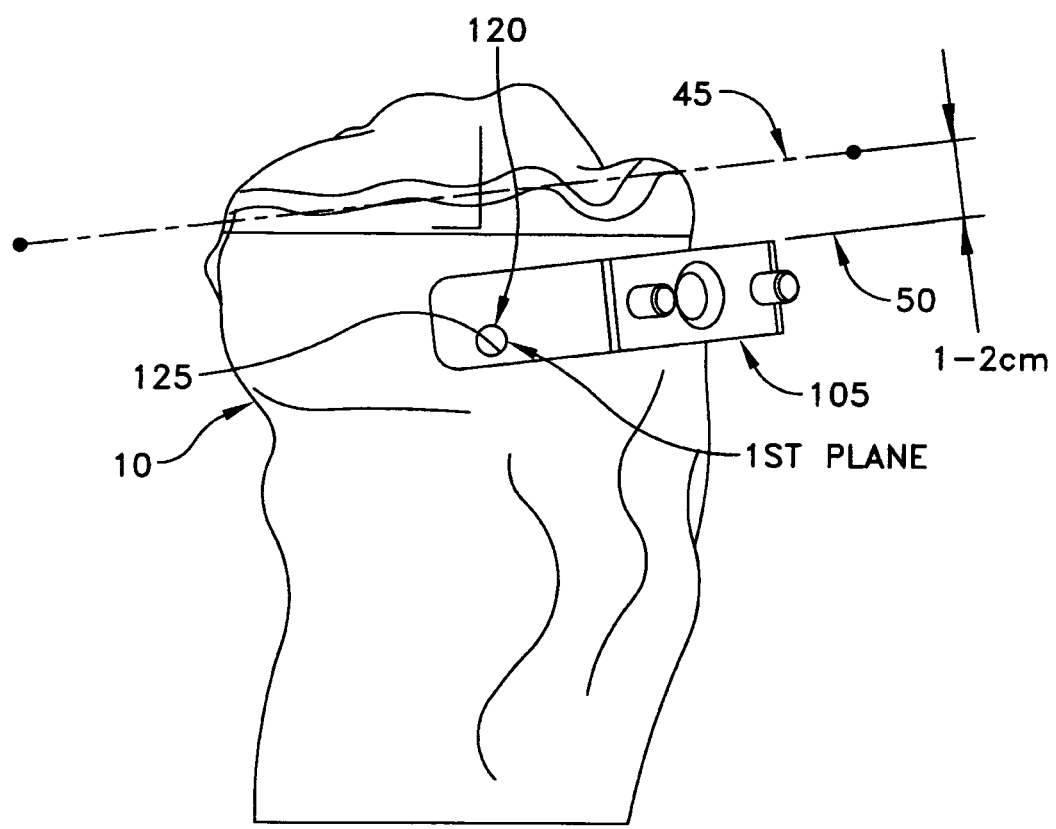

As seen in FIG. 11, the positioning guide 105 is maneuvered so that the top edge of the positioning guide is located approximately 1-2 cm below the tibial plateau. Then, a first straight pin 120 is advanced through a first bore 125 in positioning guide 105, with the positioning guide extending slightly away from the tibia so as to allow adjustment parallel to the A-P slope. Next, using a fluoroscope showing the A-P slope, positioning guide 105 is rotated until the top edge of the positioning guide is parallel to the A-P slope.

Figure 12:
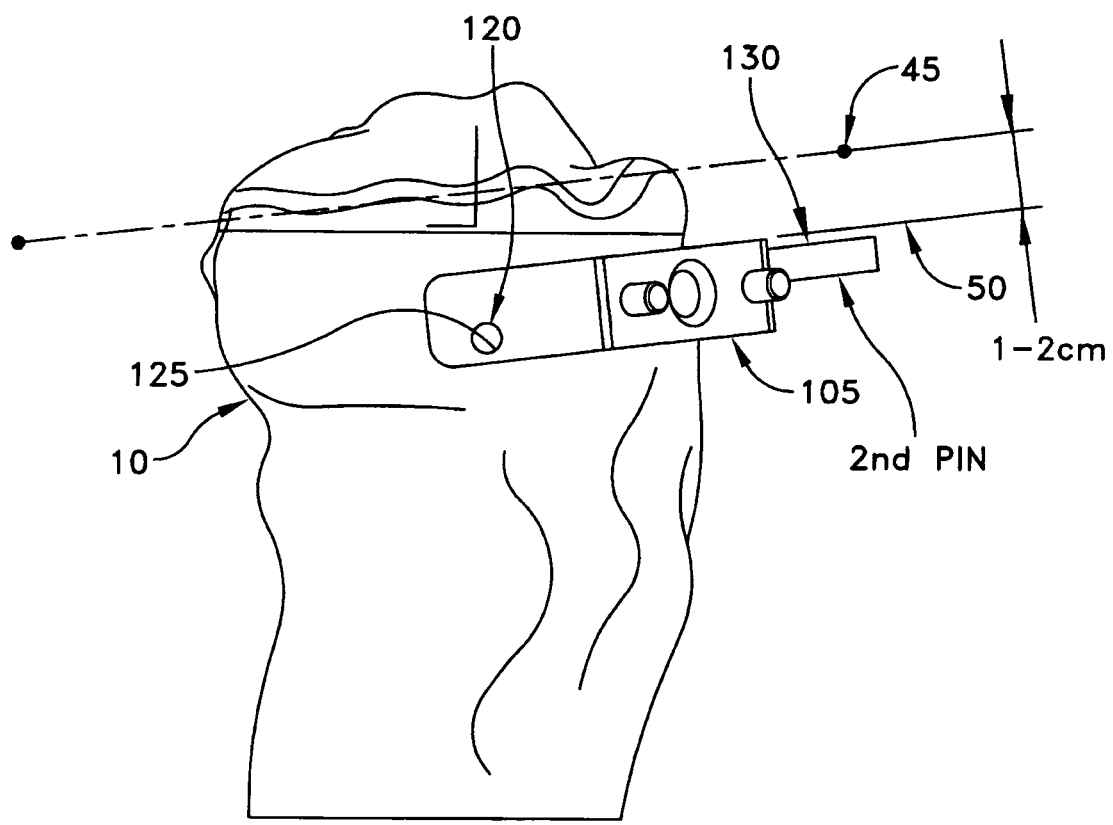
Figure 13:
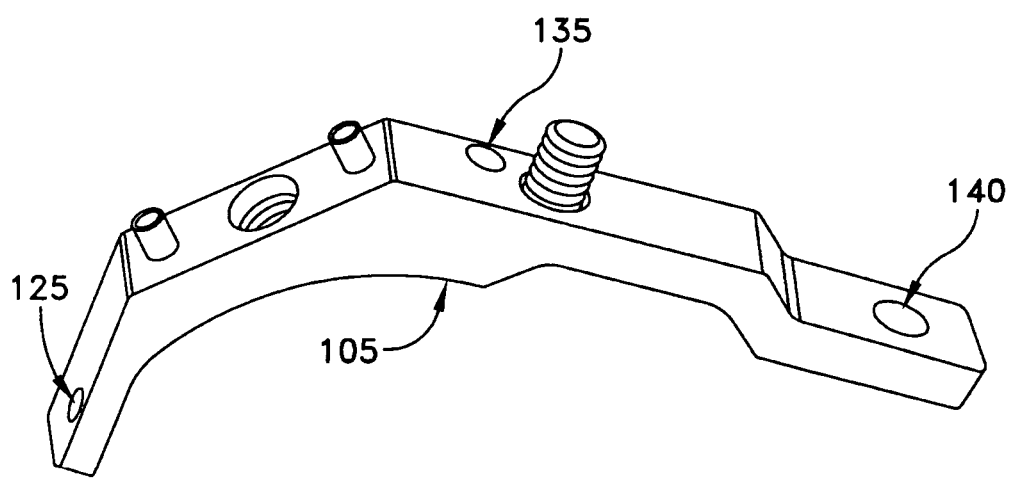
Figure 14:
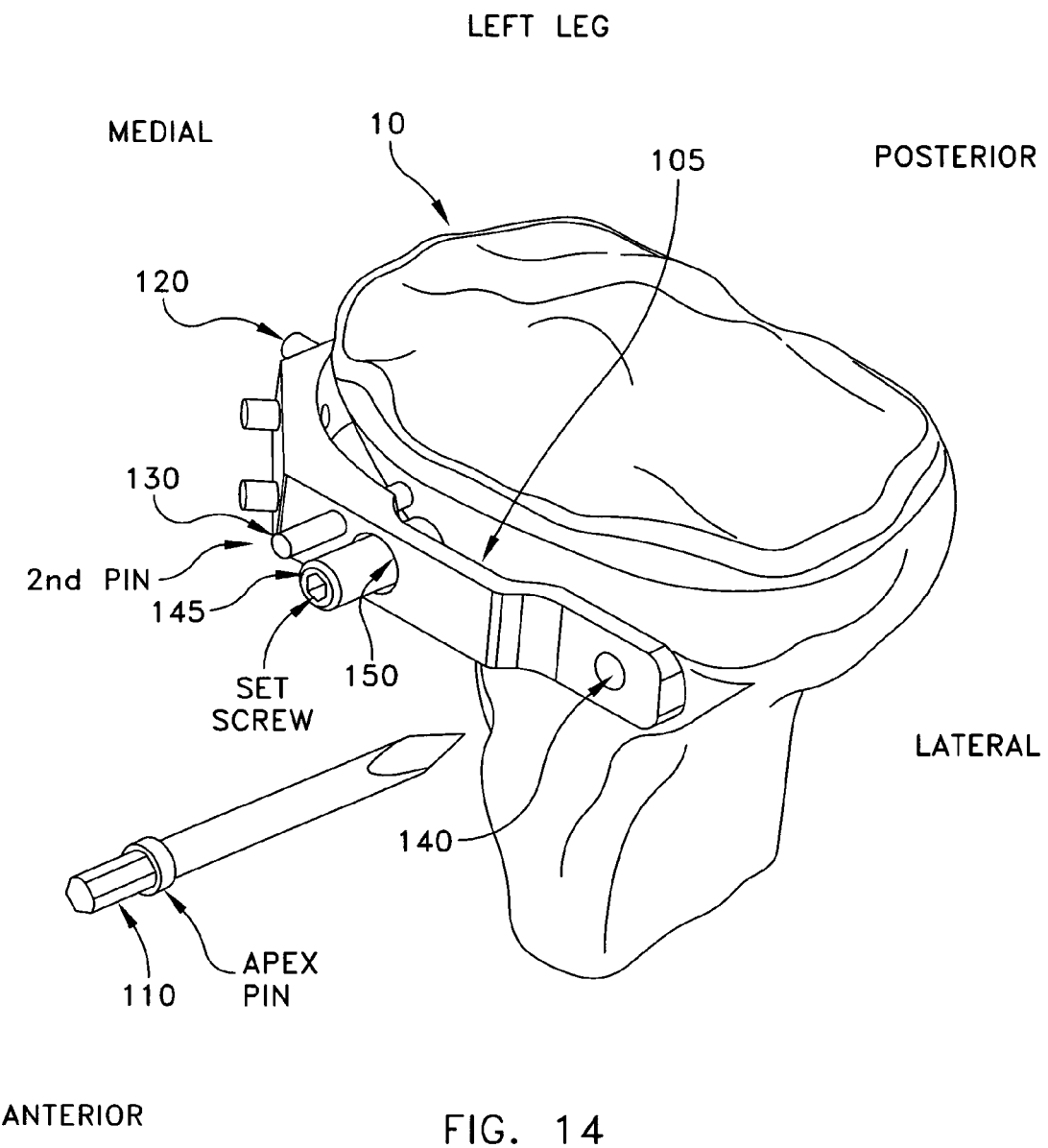
Figure 15:
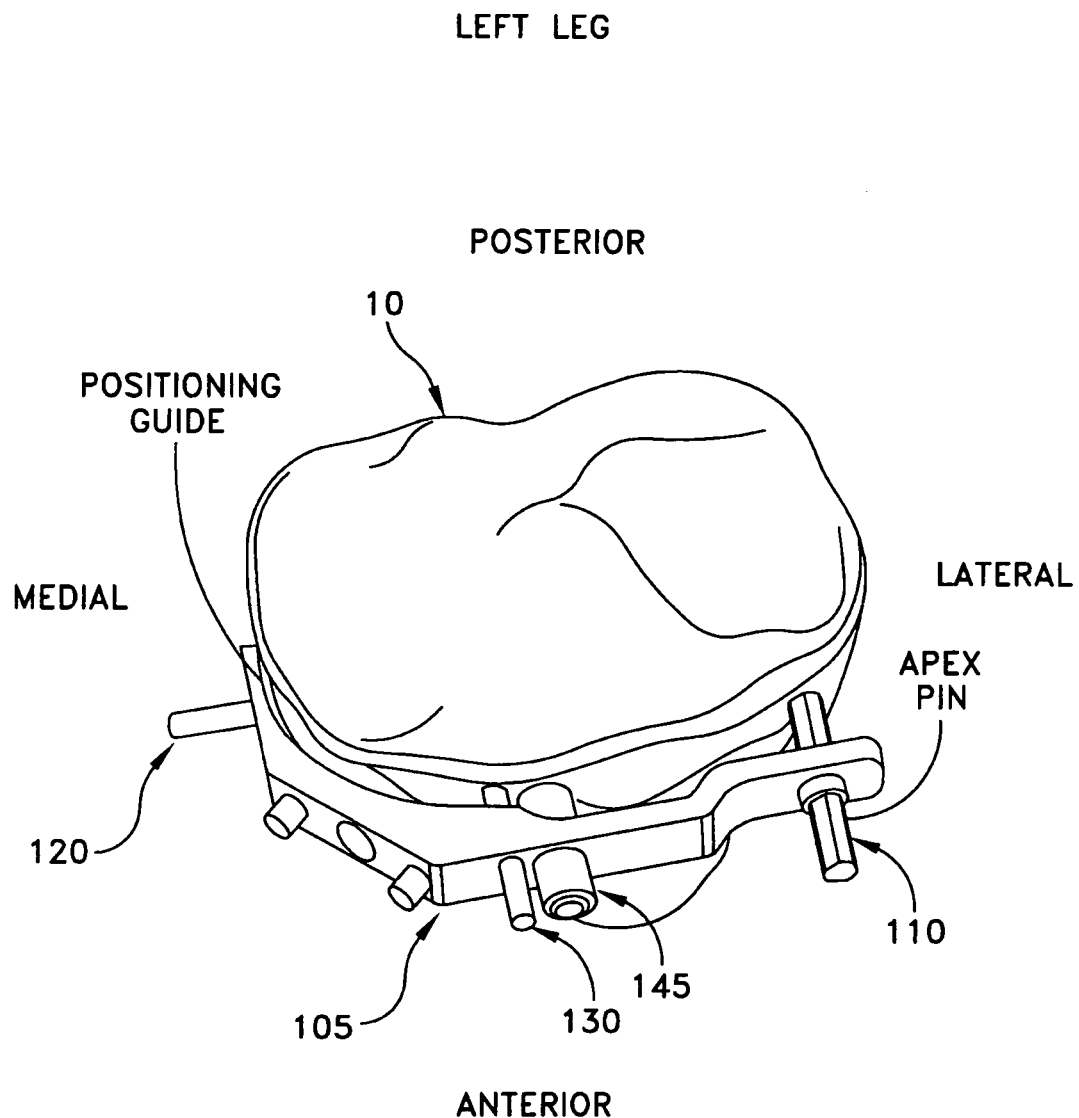
Figure 16:
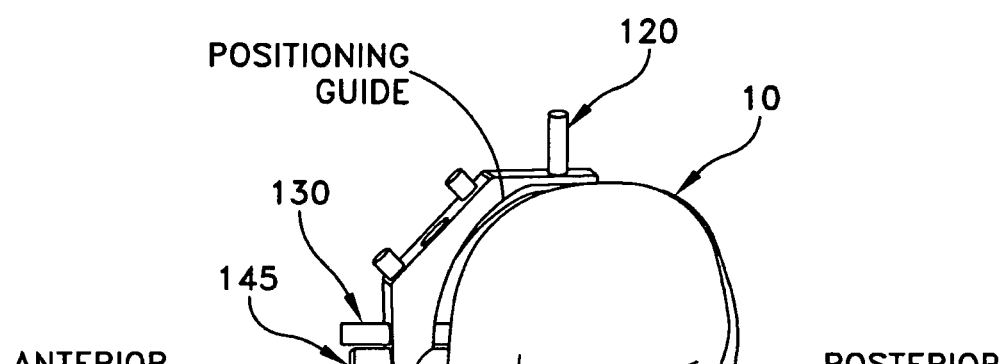
Figure 17:
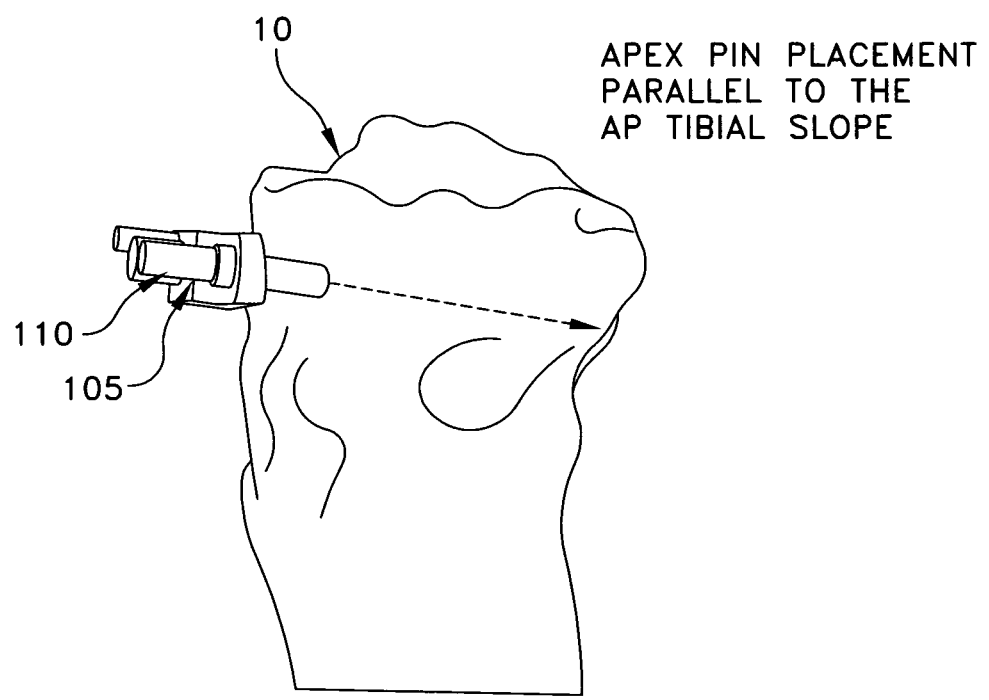

Once this has been done, and looking next at FIG. 12, a second straight pin 130 is advanced through a second bore 135 (FIG. 13) in positioning guide 105. This second pin 130 stabilizes the position of the positioning guide relative to tibia 10. It will be appreciated that, as a result of the foregoing, the positioning and placement of first and second pins 120, 130 secures positioning guide 105 relative to tibia 10 so that the top edge of the positioning guide is parallel to the A-P tibial slope. This process ensures that the apex pin bore 140 (FIG. 13) is aligned with, and defines, the axis 70 (FIG. 8) located at the intersection of A-P offset plane 50 and cut depth plane 60, which is at the far end of the osteotomy cut.

Looking next at FIGS. 14-17, apex pin 110 is then advanced through the positioning guide's apex pin bore 140 and into tibia 10. As a result, apex pin 110 extends along axis 70, i.e., at the intersection of A-P offset plane 50 and cut depth plane 60. Thus, the axis of the apex pin 110 is located at the far end of the osteotomy cut, co-planar with the plane of the osteotomy cut.

At this point, set screw 145 (FIG. 14) is advanced through set screw bore 150 and against tibia 10, so as to eliminate any remaining play in the position of positioning guide 105 relative to tibia 10. In this respect it should be appreciated that it is important not to overtighten set screw 145 during this operation so as to avoid adversely affecting the alignment of the positioning guide relative to tibia 10.

Looking next at FIGS. 18-21, cutting guide 115 is mounted onto positioning guide 105. This is done by advancing cutting guide 115 against positioning guide 105 such that the positioning guide's locating pins 155 are received through the cutting guide's holes 157. Cutting guide 115 is secured in this position by advancing a screw 160 through a bore 165 in the cutting guide and into a bore 170 in the positioning guide. This action aligns a cutting slot 175 in cutting guide 115 with the osteotomy cut plane 65 and the apex pin 110, in the sense that they are all co-planar. As a result of this action, cutting slot 175 is aligned with the plane of the desired osteotomy cut.

At this point the alignment of the cutting slot 175 is checked to ensure that it is sufficiently above the tibial tubercle 180 (FIG. 19) and below the tibial plateau 30. If cutting slot 175 is not sufficiently above tubercle 180 and below tibial plateau 30, the apparatus is removed and the foregoing operation repeated.

Figure 21:
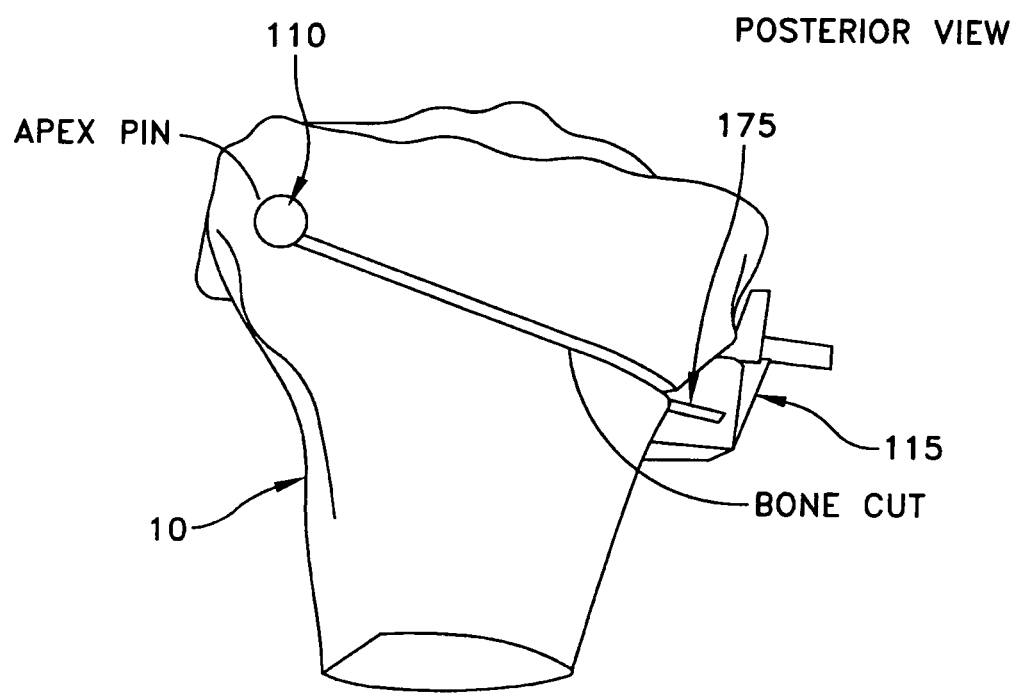
Figure 22:
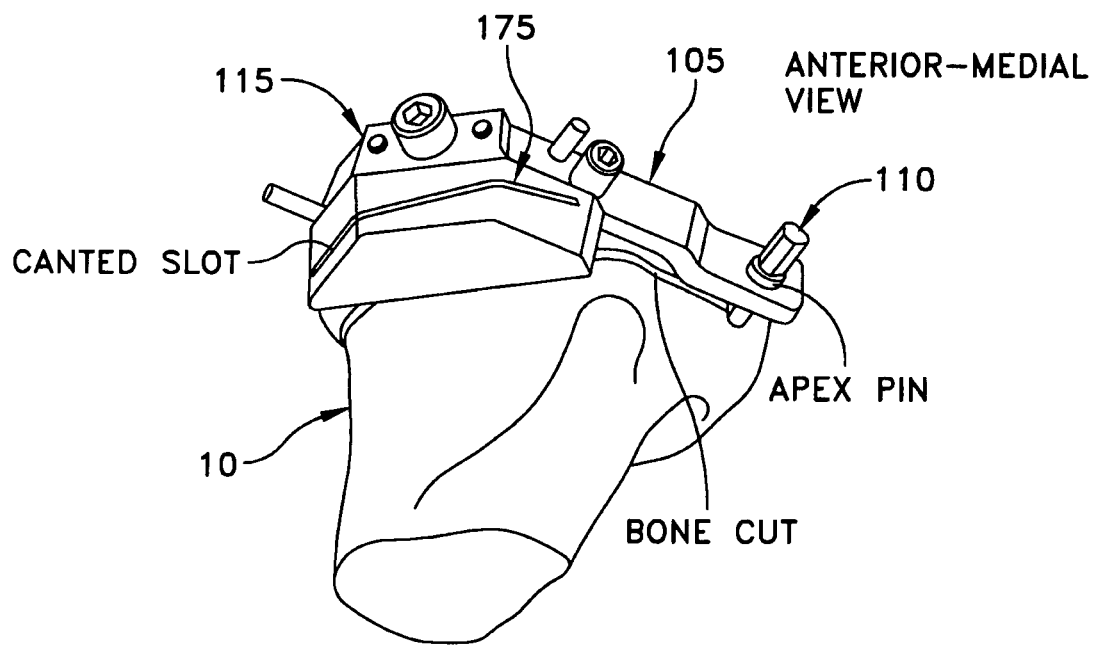
Figure 23:
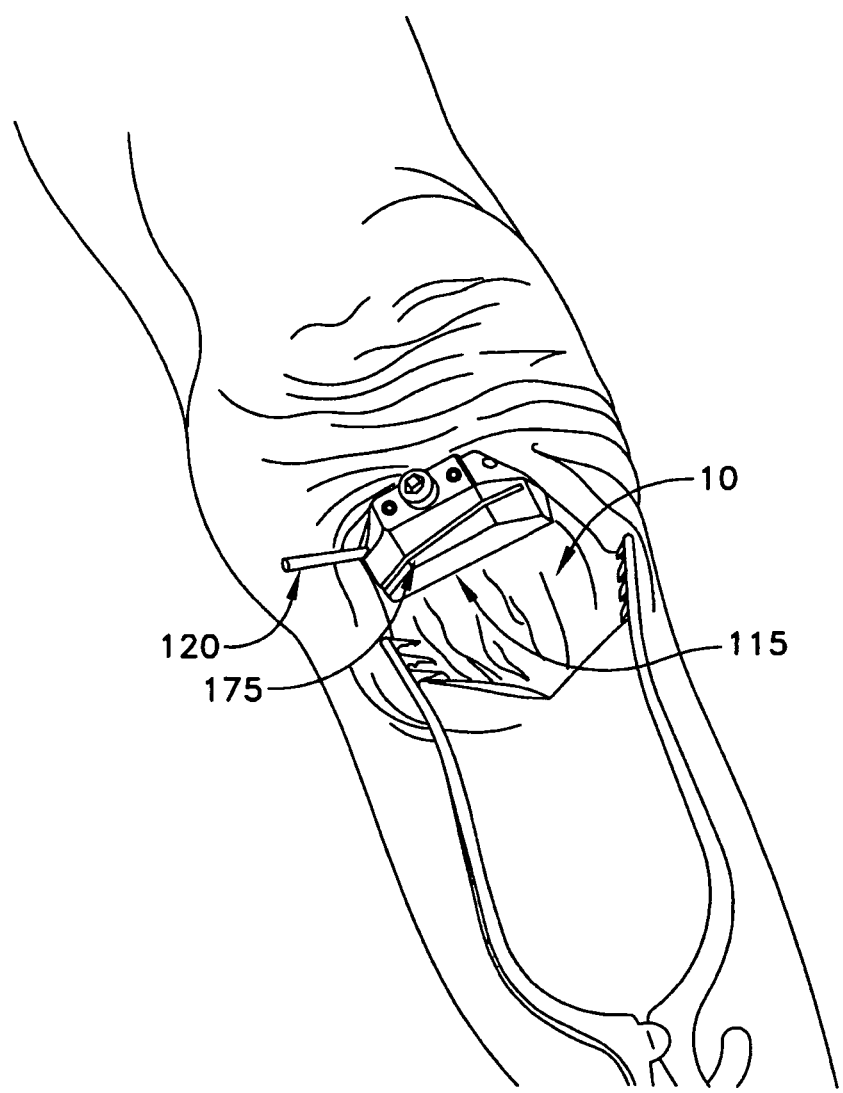
Figure 23A:
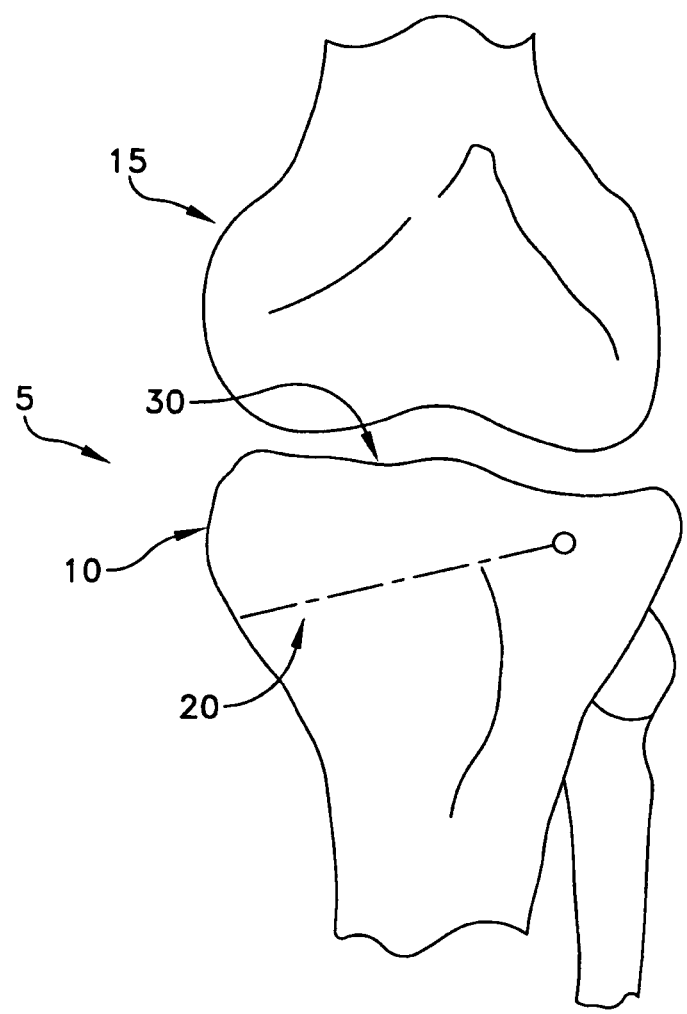
FIGS. 23A-23C show various osteotomy cuts formed in the tibia.

Looking next at FIGS. 21-23, an oscillating saw (not shown) is advanced through cutting slot 175 and into tibia 10 so as to form the desired osteotomy cut. In this respect it will be appreciated that apex pin 110 will serve as a stop to prevent the oscillating saw from overcutting the tibia and thereby damaging the portion of the tibia lateral to the osteotomy cut, which is important since this uncut bone will serve as a base or lateral hinge when the osteotomy cut is opened to form wedge-like opening in the bone. In addition, the apex pin also forms a round opening in the tibia at the base of the osteotomy cut, which will serve to relieve stress risers which may occur when the osteotomy cut is opened to form the wedge-like opening in the bone. The cut depth may be verified with a fluoroscope to ensure that the tibia is cut fully across the osteotomy cut. Then cutting guide 115, apex pin 110 and positioning guide 105 are removed, and the osteotomy cut is completed with an appropriate osteotome (not shown), using fluoroscopy to verify the cut location. See FIG. 23A, which shows the osteotomy cut 20 formed in tibia 10.

Figure 23B:
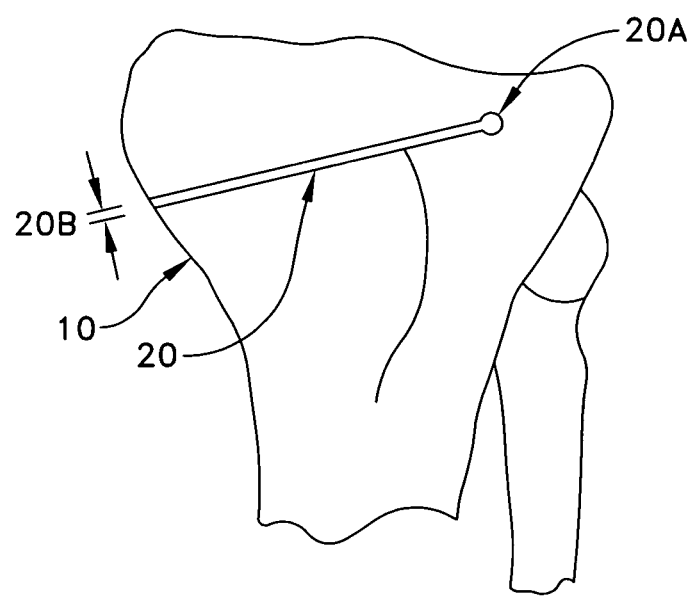

In one preferred construction, and looking now at FIG. 23B, the apex pin is sized so that the round opening 20A formed at the base of osteotomy cut 20 has a diameter larger than the thickness 20B of osteotomy cut 20.

Figure 23C:
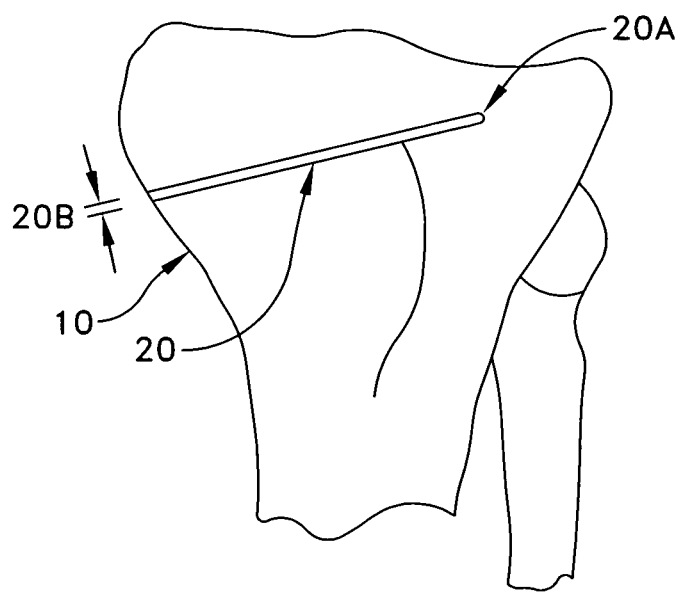

In another construction, and looking now at FIG. 23C, the apex pin is sized so that the round opening 20A formed at the base of osteotomy cut 20 has a diameter substantially the same as the thickness 20B of osteotomy cut 20.

Once the osteotomy cut has been completed (FIG. 1), the portions of the bone on either side of the osteotomy cut are moved apart as appropriate so as to form the desired wedge-like opening 25 (FIG. 2) in the bone, whereby to give tibial plateau 30 the desired orientation relative to femur 15. Then the tibia is stabilized in this position, e.g., by screwing metal plates to the bone or by inserting a wedge-like implant 35 (FIG. 3) into the opening in the bone.

Figure 24:
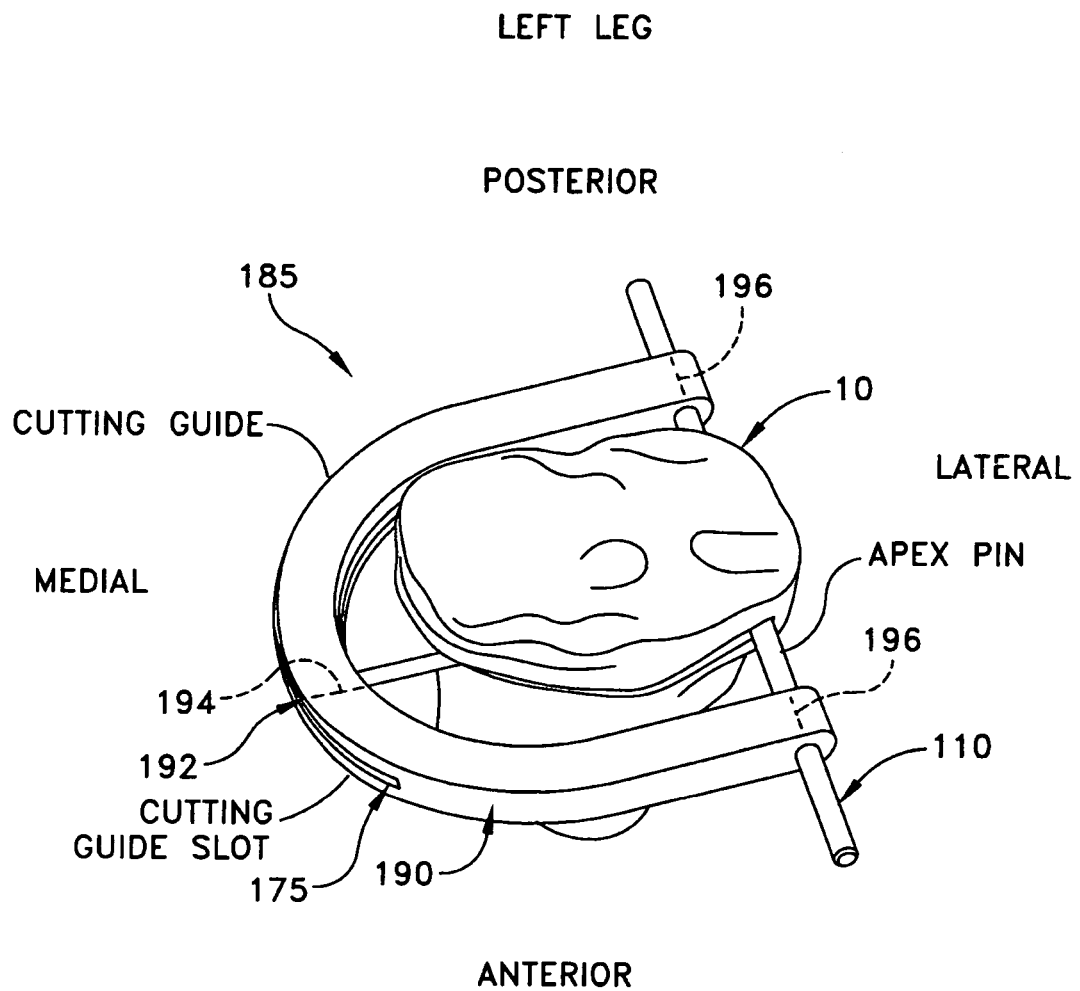
FIG. 24 shows an alternative form of the invention.

Looking next at FIG. 24, there is shown another system 185 which is intended for use in making precise and repeatable osteotomy cuts for high tibial osteotomies using an antero-medial approach. System 185 comprises a combination positioning guide/cutting guide 190 for (i) appropriately positioning apex pin 110 in tibia 10, and (ii) aligning cutting slot 175 with the designated cutting plane. This is done by first passing a positioning pin 192 through an opening 194 in the combination positioning guide/cutting guide 190, with positioning pin 192 being disposed co-planar with the designated cutting plane. Next, the combination positioning guide/cutting guide 190 is rotated about positioning pin 192 until the plane of combination positioning guide/cutting guide 190 is co-planar with the designated cutting plane. Then apex pin 110 is passed through a first opening 196 in the combination positioning guide/cutting guide 190, through tibia 10, and then through a second opening 196 formed on the far side of the combination positioning guide/cutting guide 190. This secures the combination positioning guide/cutting guide 190 in the proper position relative to tibia 10, with cutting guide slot 175 being aligned with the designated cutting plane, and with apex pin 110 disposed at the far end of the osteotomy cut. The combination positioning guide/cutting guide 190 may then be used to form the desired cut 20 (FIG. 1) in tibia 10, whereby to form the wedge-like opening 25 (FIG. 2) in the bone. Again, apex pin 110 will serve as a stop to prevent overcutting of the tibia, and will form a round opening in the tibia at the base of the osteotomy cut, which will serve to relieve stress risers which may occur when the osteotomy cut is opened to form the wedge-like opening in the bone.

Advantages of the Invention

Numerous advantages are achieved through the provision and use of the present invention.

By way of example but not limitation:

(i) the provision and use of the apex pin in conjunction with the positioning guide and cutting guide defines the lateral hinge or endpoint of the bone cut which is in specific relationship to the A-P tibial slope, which provides for the eventual opening of the osteotomy cut into a wedge void so as not to disrupt or cause inadvertent changes to the A-P tibial slope;

(ii) the apex pin acts as a positive stop for the oscillating saw blade or hand driven osteotome to prevent fracturing of the lateral cortex;

(iii) the circular diameter at the endpoint of the cutting plane effected by the apex pin reduces the stress risers that may cause intra-articular bone fracture or lateral cortex fracture during the opening of the osteotomy into a wedge void;

(iv) the cutting guide incorporates a canted or angled cutting guide slot, for use in an anterior-medial approach on the proximal tibia—the angled cutting guide slot is presented from an antero-medial location on the tibia and is aligned with the desired osteotomy cut plane;

(v) the canted slot design achieves the desired cutting plane, which is a plane that is rotated downward from the described offset plane, around an axis that is defined by the apex pin axis;

(vi) the procedure for cutting the bone (i.e., creating the osteotomy) is safe and easily reproducible from procedure to procedure; and (vii) the procedure does not adversely affect the anterior-posterior slope of the tibia.

Modifications

It will be understood that many additional changes in the details, materials, steps and arrangements of parts, which have been herein described and illustrated in order to explain the nature of the invention, may be made by those skilled in the art within the principles and scope of the invention as expressed in the appended claims.

What is claimed is:

1. A method for forming a wedge-like opening for an open wedge osteotomy comprising:
   providing a positioning guide comprising first and second orthogonal sides, the first and second orthogonal sides each terminating in distal free ends;
   securing the first and second orthogonal sides to bone such that the guide is parallel to a plane, wherein securing the first and second orthogonal sides comprises separately pinning the first and second orthogonal sides with first and second pins, respectively, proximal to the distal free ends such that the first and second pins are substantially orthogonal to each other;
   providing an apex pin and inserting the apex pin through the distal free end of the secured second orthogonal side such that an axis of the apex pin lies within the plane, in an anterior to posterior direction, and provides a single boundary line for an osteotomy cut to be made, the apex pin is dimensioned so as to provide a cylindrical opening along the plane greater in diameter than a thickness of the osteotomy cut to be made along the plane, the anterior to posterior arranged apex pin extends along the entire boundary line so as to provide (i) a positive stop along an entire length of the boundary line within the bone for limiting cutting depth, and (ii) a cylindrical opening extending along the boundary line so as to minimize the occurrence of stress risers within the bone when the bone on either side of the osteotomy cut is made and the bone is moved apart;
   affixing a cutting guide directly to the positioning guide to identify a generally anteromedial cutting plane through the bone, wherein the cutting plane intersects the plane of the positioning guide;
   cutting the bone along the cutting plane and stopping the cutting with the apex pin at the boundary line; and
   moving portions of the bone on either side of the cut apart to form the wedge-like opening for the open wedge osteotomy.

2. A method according to claim 1 wherein the bone is the tibia.

3. A method according to claim 1 wherein the bone is the tibia, and further wherein the cutting guide is configured so that the cutting plane and boundary line are determined through reference to a tibial plateau.

4. A method according to claim 3 wherein the positioning guide comprises an alignment edge, and further wherein the positioning guide and cutting guide are configured so that the cutting plane and the boundary line are correctly located when the alignment edge is properly positioned relative to an anterior-posterior slope.

5. A method according to claim 4 wherein the alignment edge comprises a top surface of the positioning guide.

6. A method according to claim 1:
   wherein the positioning guide is configured for attachment to the bone so as to establish the cutting plane and the boundary line relative to the bone; and
   wherein the cutting guide is configured for attachment to the positioning guide so as to align a cutting slot with the cutting plane.

7. A method according to claim 1, wherein the distal free end of the first orthogonal side is parallel to the first orthogonal side, and the distal free end of the second orthogonal side is parallel to the second orthogonal side.

8. A method according to claim 1, wherein affixing the cutting guide further comprises mounting the cutting guide to the positioning guide in a horizontal direction in relation to the positioning guide.

9. A method according to claim 1 further comprising advancing a set screw though the positioning guide to contact the bone.

10. A method according to claim 9, wherein advancing the set screw though the positioning guide further comprises advancing the set screw through the second orthogonal side.

11. A method according to claim 10, wherein advancing the set screw through the second orthogonal side further comprises advancing the set screw in a direction orthogonal to the first pin.

* * * * *